United States Patent [19]

Kroenke

[11] 4,406,838
[45] Sep. 27, 1983

[54] TRIOCTYLAMMONIUM MOLYBDATES

[75] Inventor: William J. Kroenke, Brecksville, Ohio

[73] Assignee: The B. F. Goodrich Company, Akron, Ohio

[21] Appl. No.: 402,480

[22] Filed: Jul. 28, 1982

[51] Int. Cl.³ .............................................. C07F 11/00
[52] U.S. Cl. ................................................. 260/429 R
[58] Field of Search ................................... 260/429 R

[56] References Cited

U.S. PATENT DOCUMENTS

| | | | |
|---|---|---|---|
| 3,223,625 | 12/1965 | Cyphers et al. | 260/429 R X |
| 3,290,245 | 12/1966 | Elliott et al. | 260/429 R X |
| 3,349,108 | 10/1967 | Marzluff | 260/429 R |
| 4,053,455 | 10/1977 | Kroenke | 260/429 R X |
| 4,153,792 | 5/1979 | Kroenke | 260/429 R X |
| 4,217,292 | 8/1980 | Kroenke | 260/429 R |
| 4,234,474 | 11/1980 | Kroenke | 260/429 R X |
| 4,235,770 | 11/1980 | Kroenke | 260/429 R X |
| 4,247,451 | 1/1981 | Kroenke | 260/429 R X |
| 4,248,766 | 2/1981 | Kroenke | 260/429 R X |
| 4,248,767 | 2/1981 | Kroenke | 260/429 R X |

Primary Examiner—Helen M. S. Sneed
Attorney, Agent, or Firm—James R. Lindsay

[57] ABSTRACT

Trioctylammonium molybdates having the empirical formula $$[(C_8H_{17})_3NH]_a Mo_b O_c$$

where a, b and c are (2, 6, 19); (6, 7, 24) or (4, 8, 26) are disclosed as novel amine molybdates which are useful as smoke retardant additives for vinyl chloride polymer compositions.

4 Claims, No Drawings

TRIOCTYLAMMONIUM MOLYBDATES

BACKGROUND OF THE INVENTION

Amine molybdates may be produced by reacting an amine or an amine salt with a molybdenum compound such as molybdenum trioxide ($MoO_3$), molybdic acid or a molybdenum salt in an acidic aqueous medium made acidic through the addition of a suitable acid such as an inorganic acid (exemplified by hydrochloric acid, nitric acid or sulfuric acid) or an organic acid containing 1 to 12 carbon atoms (exemplified by acetic acid, propionic acid, benzoic acid, and the like). The acidic mixture is refluxed, preferably while being stirred continuously, until the reaction is complete, usually for about ¼ to 4 hours.

Amine molybdates also may be produced, as described in U.S. Pat. No. 4,217,292, by reacting essentially stoichiometric quantities of molybdenum trioxide with an amine or an amine salt in an aqueous medium essentially free of acid and in which a water-soluble ammonium or monovalent metal or divalent metal or trivalent rare earth metal salt of an inorganic or organic acid is dissolved. Sometimes the reaction is carried out in a polar organic solvent instead of water.

The particular amine molybdate formed may depend upon which process is used to form the amine molybdate and the quantity of reactants present in the reaction mixture, as well as the reaction conditions.

SUMMARY OF THE INVENTION

The present invention pertains to a class of novel molybdates, namely, trioctylammonium molybdates, which may be represented by the formula:

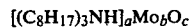

$$[(C_8H_{17})_3NH]_aMo_bO_c$$

where a, b and c are (2, 6, 19) (6, 7, 24) or (4, 8, 26). Like many other amine molybdates, the trioctylammonium molybdates function as effective smoke retardant additives for vinyl chloride polymers.

DETAILED DESCRIPTION OF THE INVENTION

Trioctylammonium molybdates may be produced by reacting ammonium dimolybdate [$(NH_4)_2Mo_2O_7$] and trioctylamine [$(C_8H_{17})_3N$] in an acidic aqueous medium. Suitable acids include inorganic acids such as hydrochloric acid, nitric acid, or sulfuric acid, or mixtures thereof. The amount of acid used may be varied widely from about ½ to 10 or more molar equivalents of acid per molar equivalent of ammonium dimolybdate. However, about a 1/1 molar equivalent ratio is preferred. Sufficient water is included in the reaction mixture to insure a reaction mixture that has a consistency that enables it to be easily stirred. The mixture is heated to reflux and refluxed for about 10 minutes to 16 hours, preferably while being stirred continuously. After the reaction is completed, the solid reaction product is separated from the aqueous medium by filtration, centrifugation, or other suitable separation procedure. The recovered solid reaction product desirably is washed with water and then is dried. The molar ratio of ammonium dimolybdate to trioctylamine will influence the trioctylammonium molybdate product formed as a result of the reaction. Theoretical molybdate/trioctylamine molar ratios from 0.5/1 to 3/1 are used. However, the actual molar ratios that can be used in the reaction can be outside the stated range.

Not all of the realizable trioctylammonium molybdates can be prepared as described above. Certain of them can be best prepared by reacting previously formed trioctylammonium molybdates with a strong inorganic acid, such as hydrochloric acid, in polar solvents such as water, methanol, and acetonitrile.

The trioctylammonium molybdates within the scope of the present invention are trioctylammonium hexamolybdates [$(C_8H_{17})_3NH]_2Mo_6O_{19}$, trioctylammonium heptamolybdates [$(C_8H_{17})_3NH]_6Mo_7O_{24}$ and trioctylammonium octamolybdates [$(C_8H_{17})_3NH]_4Mo_8O_{26}$. The following examples more fully illustrate the preparation of the novel trioctylammonium molybdates of the present invention.

EXAMPLE I 10.00 Grams of trioctylamine were added to a 500 milliliter round-bottom flask equipped with a water-cooled condenser and a mechanical stirrer. 5.58 grams of a 37 percent hydrochloric acid solution were mixed with 200 milliliters of water and were added to the flask. 9.62 grams of ammonium dimolybdate were dissolved in 50 milliliters of water and added to the flask. The mixture in the flask was heated to reflux and refluxed for 10 minutes and then was cooled to room temperature (about 25° C.). The cooled mixture was poured into a Buchner funnel. A yellowish-green residue was collected on the filter paper. The residue was washed three times with about 50 milliliters of water and dried in a vacuum oven maintained at about 65° C. for 1½ hours. Infrared analysis identified the residue to be a mixture of trioctylammonium alpha- and beta- octamolybdates.

3.12 Grams of trioctylammonium octamolybdate and 20 milliliters of acetonitrile were added to a 50 milliliter Erlenmeyer flask and stirred until the trioctylammonium octamolybdate was dispersed within the acetonitrile. 0.08 gram of concentrated sulfuric acid was mixed with 3 milliliters of water and added to the flask. The contents of the flask were warmed and stirred for 2 hours. The solid molybdate charged to the flask was converted to a light brown oily product. The contents of the flask were cooled to room temperature (about 25° C.). The acetonitrile/water layer was separated from the light brown oily layer. The oily product was washed three times with separate water washes of 20 milliliters of water, the oily layer being separated from the water wash after each wash. The oily product was dried in a vacuum oven at 40° C. for 16 hours. The dried oily product was dissolved in 20 milliliters of acetonitrile. 0.04 Gram of concentrated sulfuric acid was added to the solution and the resulting mixture was stirred for ½ hours. The mixture was rotoevaporated to dryness. A green oily product was obtained. The oily product was dried in a vacuum oven at 40° C. for 2 hours. Infrared analysis identified the product as trioctylammonium hexamolybdate containing a small amount of unreacted trioctylammonium octamolybdate.

EXAMPLE II

The trioctylammonium molybdates have been found to be a smoke retardant additive for vinyl chloride polymer compositions. When used as a smoke retardant additive, the trioctylammonium molybdates desirably either are combined with the other ingredients of the vinyl chloride polymer composition on a roll mill or added by any other convenient mixing procedure. Preferably, from about 0.1 to about 20 parts by weight of a trioctylammonium molybdate is used per 100 parts by weight of vinyl chloride polymer.

Vinyl chloride polymers with which the trioctylammonium molybdates can be used as smoke retardant additives include homopolymers, copolymers and blends of homopolymers and/or copolymers, and include chlorinated polymers thereof. The vinyl chloride polymers may contain from 0 to 50 percent by weight of at least one other olefinically unsaturated monomer. Suitable monomers include 1-olefins containing from 2 to 12 carbon atoms such as ethylene, propylene, 1-butene, isobutylene, 1-hexene, 4-methyl-1-pentene, and the like; dienes containing from 4 to 10 carbon atoms, including conjugated dienes such as butadiene, isoprene, piperylene, and the like; ethylidene norbornene and dicyclopentadiene; vinyl esters and allyl esters such as vinyl acetate, vinyl chloroacetate, vinyl propionate, vinyl laurate, alkyl acetate, and the like; vinyl aromatics such as styrene, α-methyl styrene, chlorostyrene, vinyl toluene, vinyl naphthalene, and the like; vinyl allyl ethers and ketones such as vinyl methyl ether, allyl methyl ether, vinyl isobutyl ether, vinyl n-butyl ether, vinyl chloroethyl ether, methylvinyl ketone, and the like; vinyl nitriles such as acrylonitrile, methacrylonitrile, and the like; cyanoalkyl acrylates such as α-cyanomethyl acrylate, the α-β- and α-cyanopropyl acrylate, and the like; olefinically unsaturated acids and esters thereof including α,β-olefinically unsaturated acids and esters thereof such as methyl acrylate, ethyl acrylate, chloropropyl acrylate, butyl acrylate, hexyl acrylate, 2-ethylhexyl acrylate, dodecyl acrylate, octadecylacrylate, methoxyethyl acrylate, ethoxyethyl acrylate, hexylthioethyl acrylate, methyl methcarylate, ethyl methacrylate, butyl methacrylate, and the like.

The vinyl chloride polymer, in addition to the trioctylammonium molybdate, may contain the usual compounding ingredients known to the art such as fillers, stabilizers, opacifiers, lubricants, processing aids, impact modifiers, plasticizers, antioxidants, and the like.

Smoke retardancy may be measured using an NBS Smoke Chamber according to procedures described in ASTM E662-79 "Test For Specific Optical Density Of Smoke Generated By Solid Materials". Maximum smoke density (Dm) is a dimensionless number and has the advantage of representing a smoke density independent of chamber volume, specimen size or photometer path length, provided a consistent dimensional system is used. Percent smoke reduction is calculated using the equation:

$$\frac{Dm/g \text{ of control} - Dm/g \text{ of sample}}{Dm/g \text{ of control}} \times 100$$

The term "Dm/g" means maximum smoke density per gram of material. Dm and other aspects of the physical optics of light transmission through smoke are discussed fully in the ASTM publication.

Smoke retardance may be measured quickly using the Goodrich Smoke-Char Test. Test samples may be prepared by dry blending polymer resin and smoke retardant additives. The blend is ground in a liquid nitrogen cooled grinder to assure uniform dispersion of the smoke retardant additives in the resin. Small (about 0.3 g) samples of the polymer blend are pressed into pellets about ¼ inch diameter for testing. Alternatively, test samples may be prepared by blending resin, smoke retardant additives and lubricant(s) or processing aid(s) in a blender such as an Osterizer blender. The blend is milled, pressed into sheets, and cut into small (about 0.3 gram) samples for testing. The test samples are placed on a screen and burned for 60 seconds with a propane gas flame rising vertically from beneath the samples. Sample geometry at a constant weight has been found not to be significant for the small samples used in this test. A Bernz-O-Matic pencil flame burner head is used with gas pressure maintained at about 40 psig. Each sample is immersed totally and continuously in the flame. Smoke from the burning sample rises in a vertical chimney and passes through the light beam of a Model 407 Precision Wideband Photometer (Grace Electronics, Inc., Cleveland, Ohio) coupled with a photometer integrator. Smoke generation is measured as integrated area per gram of sample.

The smoke retardant property of trioctylammonium molybdates is illustrated by the following example:

EXAMPLE III

The following recipe was used:

| Material | Parts by Weight |
|---|---|
| Polyvinyl Chloride resin* | 100.0 |
| Lubricant** | 2.0 |
| Tin Stabilizer*** | 2.0 |
| Trioctylammonium molybdate | 5.0 |

*Homopolymer of vinyl chloride having an inherent viscosity of about 0.98–1.04; ASTM classification GQ-5-15543.
**A commercial polyethylene powder lubricant (Microthene 510).
***Tin Thioglycolate 5.0 Grams of the trioctylammonium gamma-octamolybdate of Example I were mixed with 100.0 grams of the polyvinyl chloride resin of the aforesaid recipe on a two-roll mill. The lubricant and tin stabilizer of the recipe were added to the molybdate-polyvinyl chloride resin mixture and the resulting composition was milled on the mill for about 5 minutes at a roll temperature of about 165° C. The milled composition was pressed into a 6×6×0.050 inch sheet. Pressing was done at about 160° C. for 5 minutes using 40,000 pounds (about 14,900 kg) of force applied to a 4-inch ram. The sample (Sample 1) received a 2 minute preheat before being pressed.

The molded samples were cut into 2 ⅛×2 ⅛×0.50 inch sections and tested against a control sample formed utilizing the aforesaid recipe but without use of the molybdate additive. Testing was performed using the flaming mode of the NBS Smoke Chamber Test (ASTM E662-79) described hereinabove. The test results are given in Table I.

TABLE I

| Sample | Dm/g* | Smoke Reduction (%) |
|---|---|---|
| Control | 60.8 | — |
| 1 | 28.4 | 53.3 |

*Dm/g— maximum smoke density per gram of sample.

0.075 Gram of the slightly impure trioctylammonium hexamolybdate product of Example II and 1.50 grams of polyvinyl chloride resin (homopolymer of vinyl chloride having an inherent viscosity of about 0.98–1.04, ASTM classification GO-5-15543) were blended together in a nitrogen-cooled grinder. The mixture (Sample 2) was cold-pressed into ¼ inch diameter pellets weighing about 0.3 gram each.

A "control" sample was prepared by forming pellets of the polyvinyl chloride resin.

Testing was preformed using the Goodrich Smoke-Char Test described above. The test results are set forth in Table II.

TABLE II

| Sample | Spvc* | Smoke Reduction (%) |
|---|---|---|
| Control | 74.8 | — |
| 2 | 39.5 | 47.2 |

*Smoke-Char test smoke number

The improved smoke retardant vinyl chloride polymer compositions obtained by the inclusion of a trioctylammonium molybdate in the composition are useful wherever smoke reduction is a desirable property, such as in carpeting, house siding, plastic components for aircraft and passenger car interiors, and the like.

I claim:

1. Trioctylammonium molybdates having the empirical formula $$[(C_8H_{17})_3NH]_a Mo_b Q_c$$

where a, b and c are (2, 6, 19); (6, 7, 24) or (4, 8, 26).

2. The trioctylammonium molybdate of claim 1 wherein a is 2, b is 6, and c is 19.

3. The trioctylammonium molybdate of claim 1 wherein a is 6, b is 7, and c is 24.

4. The trioctylammonium molybdate of claim 1 wherein a is 4, b is 8, and c is 26.

* * * * *